US006495833B1

(12) United States Patent
Alfano et al.

(10) Patent No.: US 6,495,833 B1
(45) Date of Patent: Dec. 17, 2002

(54) SUB-SURFACE IMAGING UNDER PAINTS AND COATINGS USING EARLY LIGHT SPECTROSCOPY

(75) Inventors: Robert R. Alfano, Bronx, NY (US); Ping-Pei Ho, Great Neck, NY (US)

(73) Assignee: Research Foundation of CUNY, New York, NY (US)

( * ) Notice: Subject to any disclaimer, the term of this patent is extended or adjusted under 35 U.S.C. 154(b) by 105 days.

(21) Appl. No.: 09/598,705

(22) Filed: Jun. 21, 2000

Related U.S. Application Data

(60) Provisional application No. 60/177,144, filed on Jan. 20, 2000.

(51) Int. Cl.[7] .......................... G01N 21/88; G01N 21/47
(52) U.S. Cl. ............................... 250/341.8; 250/339.11; 250/330
(58) Field of Search .................... 250/341.8, 339.11, 250/358.1, 330

(56) References Cited

U.S. PATENT DOCUMENTS

| | | | | |
|---|---|---|---|---|
| 3,673,860 A | * | 7/1972 | Flaherty et al. | 250/358.1 |
| 5,266,806 A | * | 11/1993 | Barber | 250/341.4 |
| 5,371,368 A | * | 12/1994 | Alfano et al. | 250/341.1 |
| 5,451,785 A | * | 9/1995 | Faris | 250/330 |
| 5,719,395 A | * | 2/1998 | Lesniak | 250/330 |
| 5,799,656 A | * | 9/1998 | Alfano et al. | 250/341.1 |
| 5,847,394 A | * | 12/1998 | Alfano et al. | 250/341.1 |
| 5,905,261 A | * | 5/1999 | Schotland et al. | 2550/341.8 |
| 5,962,852 A | * | 10/1999 | Knuettel et al. | 250/339.11 |
| 6,032,070 A | * | 2/2000 | Flock et al. | 600/310 |

OTHER PUBLICATIONS

Wang et al., "Ballistic 2–D Imaging Through Scattering Walls Using an Ultrafast Optical Kerr Gate," Science, vol. 253, pp. 769–771, Aug. 1991.
Alfano et al., "Time–Resolved Imaging of Translucent Droplets in Highly Scattering Turbid Media," vol. 264, pp. 1913–1915, Jun. 1994.
Wang et al., "Time–Resolved Fourier Spectrum and Imaging in Highly Scattering Media," Applied Optics, vol. 32, No. 26, pp. 5043–5048, Sep. 1993.
Ho et al., "Snake Light Tomography," Optics & Photonics News, pp. 23–27, Oct. 1993.

(List continued on next page.)

*Primary Examiner*—Constantine Hannaher
*Assistant Examiner*—Albert Gagliardi
(74) *Attorney, Agent, or Firm*—F. Chau & Associates, LLP

(57) ABSTRACT

A system for non-destructively imaging surfaces through a coating, in accordance with the present invention, includes a near-infrared (NIR) light source for illuminating a coated surface. A detector is positioned in an operative relationship with the NIR light source to receive light backscattered from the coated surface and from the coating. A gating device is positioned in an operative relationship with the detector to selectively permit light to pass to the detector to measure optical characteristics of the backscattered light such that determinations of a state of a surface below the coating is determined based on the optical characteristics of the backscattered light. Methods for performing the non-destructive imaging of the present invention are also disclosed.

52 Claims, 9 Drawing Sheets

OTHER PUBLICATIONS

Kalpaxis et al., "Three–Dimensional Temporal Image Reconstruction of an Object Hidden in Highly Scattering Media by Time–Gated Optical Tomography," Optics Letters, vol. 18, No. 20, pp. 1691–1693, Oct. 1993.

Wang et al., "Fourier Spatial Filter Acts as a Temporal Gate for Light Propagating Through a Turbid Medium," Optics Letters, vol. 20, No. 13, pp. 1498–1500, Jul. 1995.

Demos et al., "Temporal Gating in Highly Scattering Media by the Degree of Optical Polarization," Optics Letters, vol. 21, No. 2, pp. 161–163, Jan. 1996.

Guo et al., "Second–harmonic Tomography of Tissues," Optics Letters, vol. 22, No. 17, pp. 1323–1325, Sep. 1997.

Ho et al., "Time–gated Images of Calcification Regions in Turbid Media," SPIE, vol. 2979, pp. 94–97, Feb. 1997.

Zeylikovich et al., "Ultrafast Correlation Interferometric Imaging Through a Moving Scattering Medium," Optics Communications, vol. 135, pp. 217–222, 1997.

K. Yoo et al., "Time–resolved coherent and incoherent components of forward light scattering in random media", Optical Society of America, 1990.

* cited by examiner

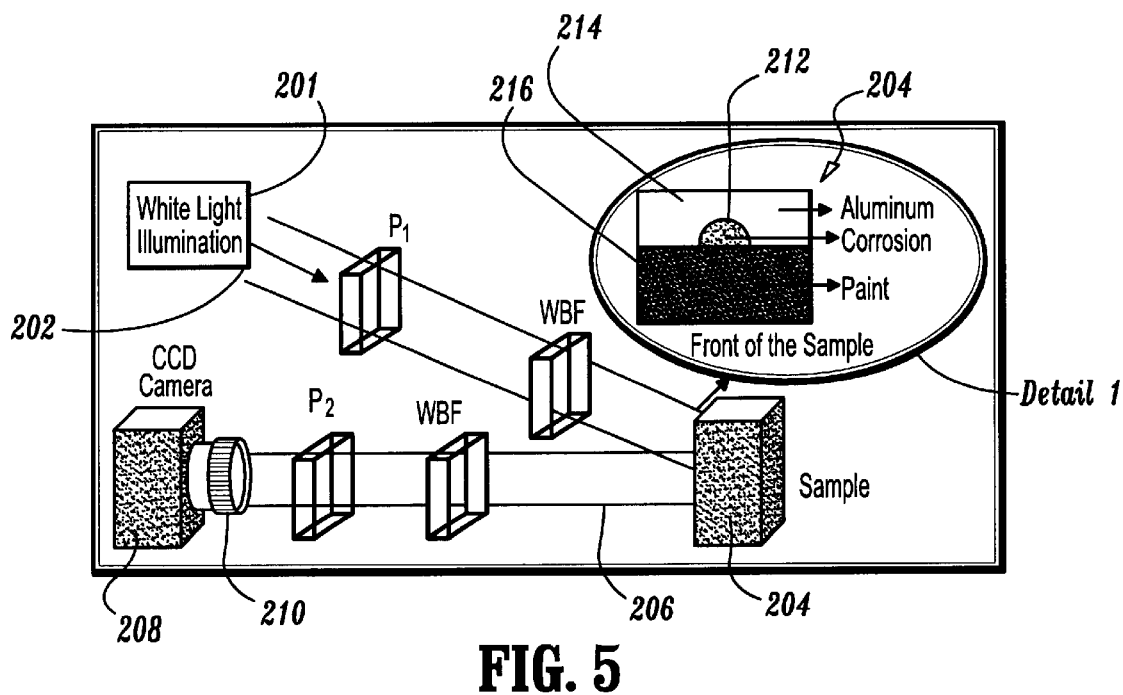
FIG. 5
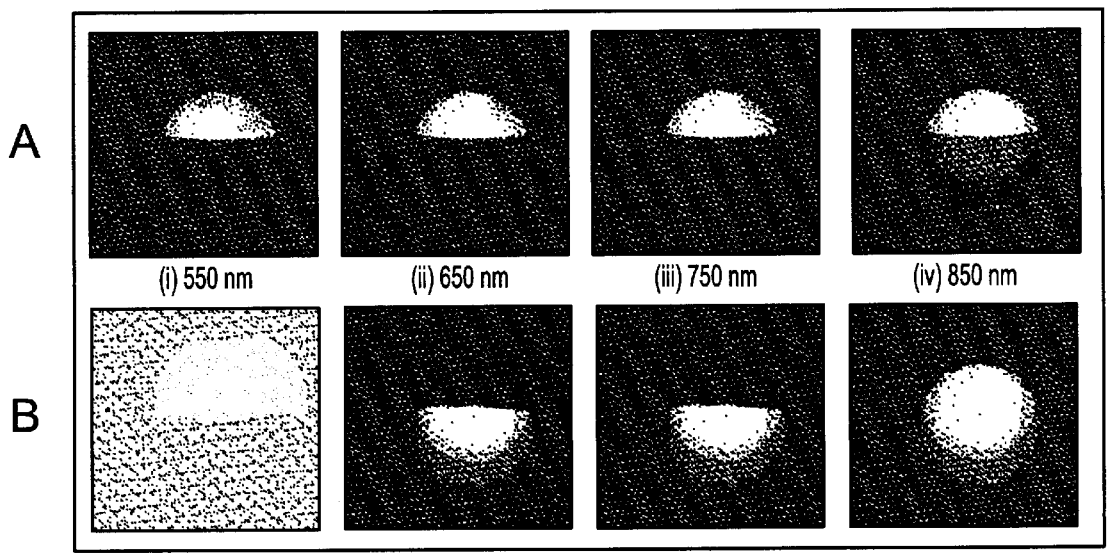
FIG. 6A  FIG. 6B  FIG. 6C  FIG. 6D
(i) 550 nm  (ii) 650 nm  (iii) 750 nm  (iv) 850 nm
FIG. 7A  FIG. 7B  FIG. 7C  FIG. 7D

SUB-SURFACE IMAGING UNDER PAINTS AND COATINGS USING EARLY LIGHT SPECTROSCOPY

This application claim the benefit of Provisional application No. 60/177,144 filed Jan. 20, 2000

GOVERNMENTAL INFORMATION

This invention was supported in part by CAT of New York State Science and Technology Foundation.

BACKGROUND

1. Technical Field

This disclosure relates to spectroscopy, and more particularly, to systems and methods for detecting or determining characteristics of materials under paints or coatings by employing early light spectroscopy.

2. Description of the Related Art

Paint or other coatings are typically applied to surfaces to protect the surfaces against corrosion or other damage. In some instances corrosion, cracking or other damage begins under the paint or coating and is undetectable by visual inspection. Inspections may be carried out by one or more of the following non-destructive imaging (NDI) techniques.

Ultrasonic (pulse echo or through transmission) methods can monitor larger defects of, for example, aircraft structures for a whole-field but are not preferred for detection of early or surface deterioration. The techniques are particularly conducive to rapid imaging of a surface and include magneto-optic eddy current imaging, active thermograph, optically aided visual inspection, and spectral imaging.

Magneto-optic imaging (MOI) can image corrosion and cracks over a small area the size of the magneto-optic crystal plate used in a hand-held scanner. However, MOI's sensitivity to top-surface corrosion depends on the degree to which the eddy currents are altered and gives rise to anomalies in the induced magnetic field at the surface. It has not been shown conclusively that the MOI technique can detect incipient corrosion that has not yet produced a significant increase in macroscopic surface roughness.

Active Thermography (AT) is an increasingly important technique for detecting subsurface flaws such as delamination, debonding, and second-surface corrosion. AT has a lower sensitivity to incipient corrosion under paint; however, because (1) the initial stages of corrosion do not significantly increase the thermal impedance of the surface compared to a layer of paint alone, and (2) the detailed resolution of incipient corrosion effects at the top surface requires a very high speed infrared camera to resolve surface transients which may appear only in the few milliseconds after the initial flash lamp illumination. Such equipment is prohibitively expensive for use on a wide scale. However, for significant surface corrosion, AT and MOI have the potential to image significant surface corrosion damage and distinguish it from subsurface effects by employing commercially available instrumentation.

Visual Inspection (VI) is used to determine the extent of corrosion damage on a skin of a surface and around fasteners, for example, after the paint or coating has been stripped. As a nondestructive technique for painted aircraft, visual techniques are not amenable to detection of chemical changes or micro-roughness at the paint/metal interface, unless significant corrosion products penetrate through the thickness of the paint. Specialized primers and paints, which incorporate taggants, are still in the research stage and not in general use.

Spectral Imaging (SI) techniques use a compact multi-spectral imaging sensor. This method is based on the partial transparency of many aircraft paints to specific bands of infrared radiation. Using this method, it is possible to detect changes in the chemistry of the metal surface or the primer by analyzing the amplitude of reflected and emitted radiation at specific wavelengths. The layered depth information cannot be deduced from a simple SI approach, however.

Therefore, a need exists for a system and method for inspecting surfaces through a coating, such as paint. A further need exists for such a system and method, which improves upon existing techniques and does not suffer from the disadvantages as described above.

SUMMARY OF THE INVENTION

The present invention includes near infrared (NIR) optical imaging systems and methods to non-destructively image (NDI) deteriorations or defects in painted metals and artwork beneath painted surfaces are disclosed. Back-scattered light is used to determine its suitability to monitor corrosion and cracking in metal beneath paints, up to a thickness of about 500 $\mu$m. NIR light, in the paint transmission zoning spanning from 800 nm to 10,000 nm can be used to assess the quality of metallic structures below the paint level for incipient and advanced stages of corrosion and cracking. NIR light scattered from paint, corrosion, air voids, and metal can be spatially imaged in micrometers sliced sub-surface layers. Art work below a painted overcoat can be imaged and detected. Spectral, temporal, spatial, nonlinear optical, and polarization gates are employed to distinguish phantoms in turbid media, such as painted corroded metal and cracked specimens: such as painted surfaces from airplanes, submarines, ships, automobiles, and bridges.

In a layered paint-metal medium, the paint acts as a highly scattered pigmented medium where high scattering occurs. Transmission windows exist in NIR region. The metal acting as flat mirror reflects the scattered light. When corrosion or cracking is present, the smooth metal becomes microscopic irregular, which adds scattering and time delay of the probing light.

A system for non-destructively imaging surfaces through a coating, in accordance with the present invention, includes a near-infrared (NIR) light source for illuminating a coated surface. A detector is positioned in an operative relationship with the NIR light source to receive light backscattered from the coated surface and from the coating. A gating device is positioned in an operative relationship with the detector to selectively permit light to pass to the detector to measure optical characteristics of the backscattered light such that determinations of a state of a surface below the coating is determined based on the optical characteristics of the backscattered light.

A method, in accordance with the present invention, for non-destructively imaging surfaces covered by a coating includes the steps of irradiating a coated surface with near-infrared light to provide backscattered light from the coating and the coated surface, gating the backscattered light to selectively permit early light to pass to a detector, and measuring optical characteristics of the early light received by the detector to image the coated surface below the coating to determine if damage exists on the coated surface.

These and other objects, features and advantages of the present invention will become apparent from the following detailed description of illustrative embodiments thereof, which is to be read in connection with the accompanying drawings.

BRIEF DESCRIPTION OF DRAWINGS

This disclosure will present in detail the following description of preferred embodiments with reference to the following figures wherein:

FIG. 5 is an arrangement for employing polarization difference imaging (PDI) to measure the under-layer information under paints using wavelength and polarization in accordance with the present invention;

FIGS. 6A–D depict experimental results of PDI images as a function of illumination wavelength and polarization in accordance with the present invention;

FIGS. 7A–D depict experimental results of PDI images as a function of illumination wavelength and a different polarization than FIG. 6 in accordance with the present invention;

DETAILED DESCRIPTION OF PREFERRED EMBODIMENTS

Figure 1:
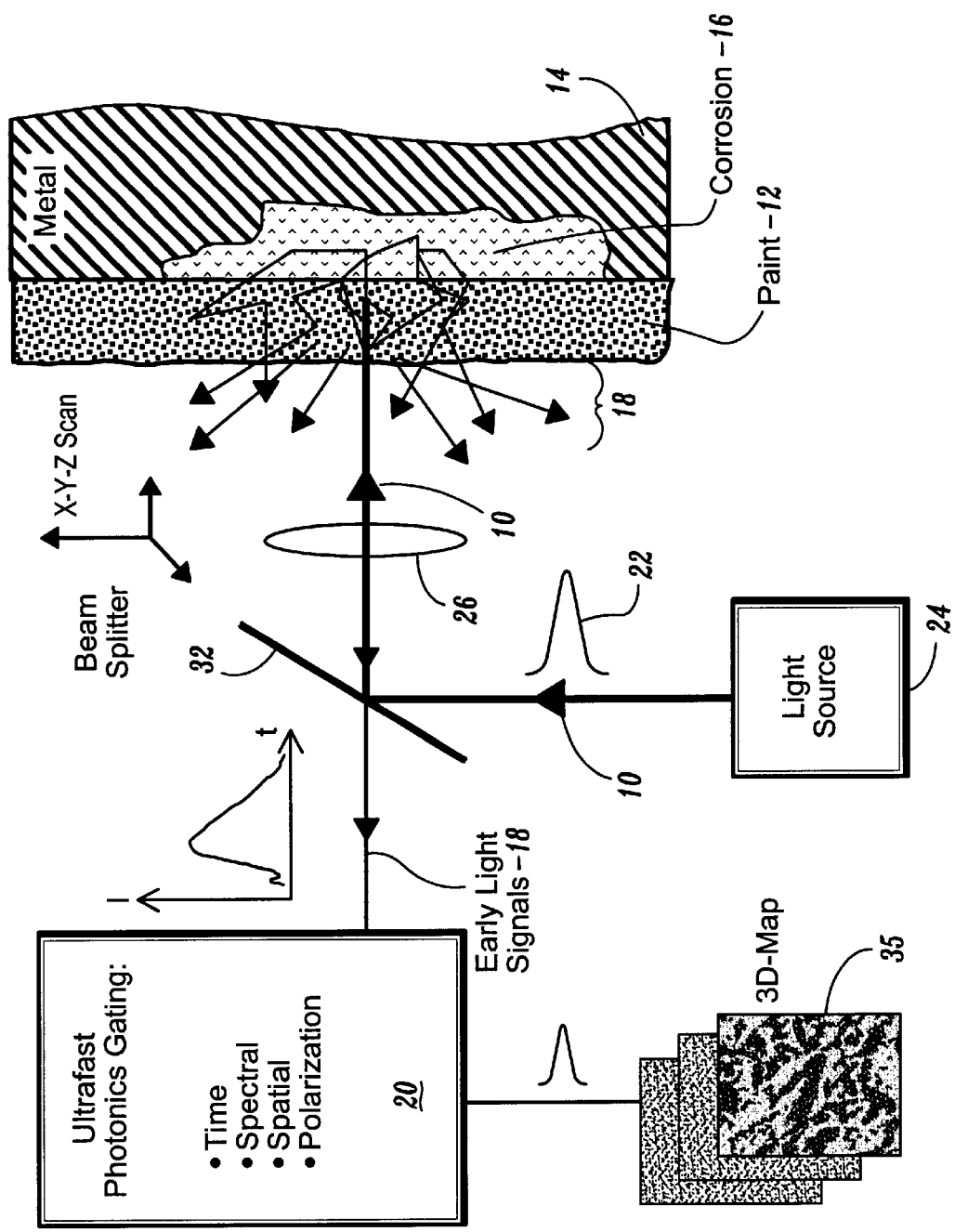
FIG. 1 is a schematic diagram of an NIR early light imaging technique to detect metal corrosion and cracking beneath painted layers in accordance with the present invention.

The present invention provides near infrared (NIR) optical imaging methods to non-destructively image (NDI) deterioration or defects in painted metals and/or artwork beneath painted surfaces are disclosed. The present invention will be described in terms of metal inspections below paints; however, this application is merely illustrative of the present invention. The present invention is broader and covers imaging techniques employed for inspecting other materials with other types of coating formed on the materials. Back-scattered light is employed to determine its suitability to monitor corrosion and cracking in metal beneath paints, up to a thickness of about 500 $\mu$m. NIR light, in the paint transmission zone spanning from 800 nm to 10,000 nm is preferably used to assess the quality of metallic structures below the paint level for incipient and advanced stages of corrosion and cracking.

NIR light scattered from paint, corrosion, air voids, and metal can be spatially imaged in micrometer-sliced subsurface layers. Art work below a painted overcoat can be imaged and detected. Spectral, temporal, spatial, nonlinear optical, and polarization gates are employed to distinguish phantoms in turbid media, such as painted corroded metal and cracked specimens: such as painted surfaces from airplanes, submarines, ships, automobiles, bridges, etc.

In a layered paint-metal medium, the paint acts as a highly scattered pigmented medium where high scattering occurs. Transmission windows exist in the NIR region. The metal, acting as flat mirror, reflects the scattered light. When corrosion or cracking is present, the smooth metal becomes microscopically irregular which adds scattering and time delay to the probing light.

Measurements on painted metals have demonstrated the feasibility of applying a NIR photonic system for detecting, for example, deteriorating metal, under paints. Advantageously, the chemical and structural changes, and the corrosion rate behind painted surfaces can be identified using NIR laser systems with wavelengths from about 800 nm to about 10,000 nm. Several optical and laser systems are disclosed for scanning and collecting arrangements from several spectral signals.

Using time-resolved methods, three main optical properties of layered structures are employed for early light imaging of hidden objects (e.g., corrosion, cracking) and surroundings (e.g., paints, metal). These optical properties include transport length, $l_t(\lambda)$, scattering coefficients, $l_s(\lambda)$, and absorption coefficients, $l_a(\lambda)$, which are determined and employed for imaging. The $l_t(\lambda)$, $l_s(\lambda)$, and $l_a(\lambda)$, are a function of wavelength of the target samples: paints, metal, alloys, and metal oxide and are determined in accordance with the invention.

The present invention obtains fundamental information on parameters from objects with incipient metal corrosion and cracking beneath paints. In one embodiment, a method provides approximately 1 $\mu$m spatial accuracy to measure image area and depth with a quasi-real-time display mode from an image of area greater than 1" by 1" per second, using a hand-held detector and portable back-up system.

Some features of the photonic NDI (non-destructive diagnostic imaging) system of the present invention include:

Detection of initial stages of corrosion and cracking under paint with the thickness of thin films from about 0.1 microns to about 1000 microns;

Determination of corrosion rates by measuring depth of corrosion to obtain the rate of corrosion formation;

Displaying image data (e.g., 1 Megabyte; 1000×1000 pixels) from an area of about 1"×1" per second on an in-situ computer monitor in quasi-real time mode;

Employing a continuous light (cw) source and spectral imaging to image an area of approximately 3 ft. ×3 ft. with a resolution that depends on the focal plane array. Much larger areas may also be imaged. For example, using ultrafast time gating, an imaging or scanned area of 12 ft. ×12 ft. can be acquired at a rate of about 1"×1" per second with a spatial resolution about 0.001"; and Provides a compact hand-held optical detection head, which attaches to a movable optical and computer cart. The dimension of the back-up laser system and computer is preferably less than about 3' by 3' by 3' and may be mounted on a roller cart for easy transportation. Regular household 120V/15A electrical power is preferably employed.

Painted metal surfaces of aircrafts are one application for the present invention. Since aircraft surfaces are most exposed to harsh environments, painted metal is highly subjective to corrosion as a result of moisture penetration through paint or through damaged areas of the coating. Corrosion beneath paint can originate from, as well as spread to, seams and fasteners, and penetrate to deeper structures. Periodic repainting of a whole aircraft is expensive and time consuming. Also, such procedures result in enormous contamination of the environment by toxic solvents as well as the old paint layers stripped from the aircraft. Corrosion detection under paint is one objective of NDI technologies.

An in-situ early light imaging technology has been developed to provide inspection monitoring in real-time and in a cost-effective way. The present disclosure review NIR early light methods for the real-time remote sensing of incipient metal corrosion and cracking beneath paints, provides a fundamental understanding of light interaction within the highly scattered paints, corroded materials, and metal surfaces. Art work below a new painting can be imaged using these spectroscopic methods.

Referring now in specific detail to the drawings in which like reference numerals identify similar or identical elements throughout the several views, and initially to FIG. 1, a schematic diagram showing principles of NDI optical imaging and scanning system is shown. NIR light 10 is sent through a paint layer or coating 12 to metal 14 which includes portion 16 which may include deteriorated metals or art work (graphic or letters) which are to be deciphered. Paint layer(s) 12 may include color pigments and $TiO_2$ scatters. Early arriving back-scattered light 18 can be time, spatial, spectral, and polarization gated to acquire information behind the scattered walls (e.g., paint). Gating is preferably controlled by a photonics gating module 20. Gating module 20 includes a detector, and a processor. The gating function of gating module 20 will be described in greater detail hereinbelow. Maps 35 of metal surfaces are provided at different depths into metal 14.

A light source 24, such as a laser, propagates a pulse or pulses 22. Laser pulses preferably include a femtosecond (fs) laser pulse which enters a beam splitter 28, which splits the laser pulse so that a portion is sent to gating control 20, and a portion is focused by a lens 26 to a scattered medium. When entering the scattered medium (e.g., paint 12), laser light undergoes a breakup into three components ballistic, snake, and diffusive, as described in "Ballistic 2-D imaging through scattering wall using an ultrafast optical Kerr gate", L. Wang, P. Ho, C. Liu, G. Zhang, R. R. Alfano, Science, 253, 769 (1991) and in "Time-resolved imaging of translucent droplets in highly scattering media", R. R. Alfano, X. Liang, L. Wang, P. P. Ho, Science, 264, 1913 (1994). These three components arrive at the detection system at different times and can be separated with ultrafast time gates of gate control 20. Ultrafast gating includes from about 10 fs to about 100 ps (fs=$10^{-15}$ seconds and ps=$10^{-12}$ seconds). Light sources employed with the present invention may include nanosecond, picosecond or femtosecond sources. Examples of picosecond and femtosecond laser sources include: mode-locked (ML) Ti:sapphire lasers, ML Forsterite lasers, ML Cunyite lasers, second-harmonic-generation from Cunyite lasers and Forsterite lasers, and optical parametric amplification from Ti:sapphire lasers. Examples of nanosecond laser sources include: diode pumped YAG lasers, diode pumped YLF lasers, diode pumped YSGG lasers, Q-switched diode lasers, second-harmonic-generation of Q-switched, YAG, YLF, YSGG lasers, and optical parametric amplification from YAG, YLF and YSGG lasers.

Figure 2B:
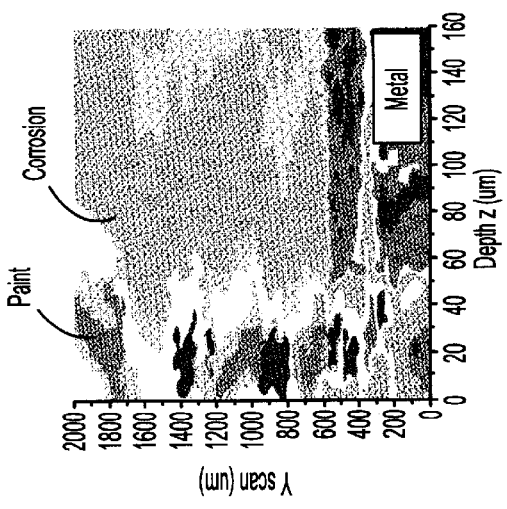
FIG. 2B depicts second harmonic generation tomography (SHGT) of a corroded steel plated covered with paint using a femtosecond Ti:sapphire laser where a pseudo color intensity chart is used to identify the measured intensity levels in accordance with the present invention.

The present invention advantageously employs NIR polarization, spectral, Kerr gate, second harmonic generation (SHG), and optical coherence tomography (OCT), and methods for on painted metals to determine incipient corrosion beneath painted surfaces. For example, a fs SHG tomography measurement of a corroded steel plate covered with paint is displayed in FIG. 2. More details of the SHGT method will be discussed below.

Figure 2C:
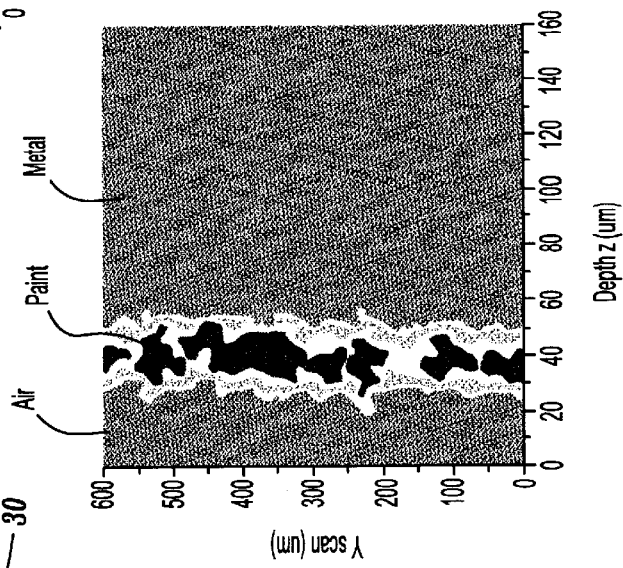
FIG. 2C depicts second harmonic generation tomography (SHGT) of an uncorroded steel plated covered with paint using a femtosecond Ti:sapphire laser where a pseudo color intensity chart is used to identify the measured intensity levels in accordance with the present invention.
Figure 2A:
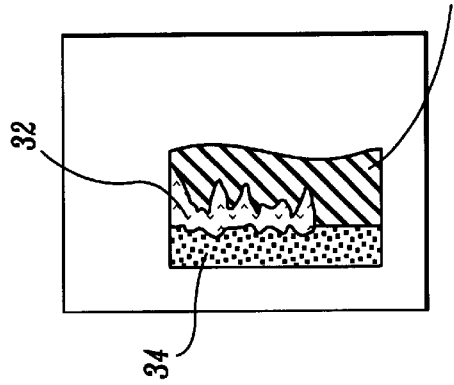
FIG. 2A is a schematic diagram of cross-section of a metal sample covered with paint used in a measurement in accordance with the present invention.

Referring to FIG. 2A, a schematic diagram of the corroded metal is displayed. A steel plate 30 includes a corroded portion 32 below a layer of paint 34. SHG signals were employed, in accordance with the present invention, from different layer depths in structures of paint 34, corroded metal 32, and metal 30 can be clearly seen as separated in FIG. 2B, with an XZ segmented layer and ~15 μm depth spatial resolution. The pseudo color display indicates the paint has the highest SHG signal, followed by corrosion, and the weakest metal and air signals. Total depth probed is ~160 μm. The spatial distribution of the corrosion depth (z) along the x-direction is quite random, and varies from about 0 μm (no corrosion) to about 100 μm. In FIG. 2C, the measurement of a reference (flat, no corrosion) metal covered with paint is displayed. The interface between paint and metal is quite uniform (δz~±10 μm), and can be as low as about 0.1-μm pending on the focal depth of the imaging lens (e.g., lens 26 of FIG. 1) used.

The disclosed NIR photonic imaging approaches offer many advantages over other existing techniques to detect incipient and advanced metal corrosion and cracking, and hidden network, some advantages include:

true 3D image of corrosion with <1 μm layer spatial resolution, determination of metallic corrosion rate from the corrosion thickness measurements, quasi-real-time display for a large area of inspection, portable capabilities, e.g., hand-held inspection unit;

provides fundamental understanding of the corrosion process, including chemical properties;

detects hidden artwork (graphics and letters) over coated materials, such as paints, paper, dielectrics, etc.; and detects corrosion, cracking, and defects of objects located on a metal and/or inside a metal or dielectric with over-coated layers, such as paints.

Four NDI photonic techniques, using time, spectral, spatial, and polarizing approaches may be combined with various gating arrangements in accordance with the present invention. NIR cw (constant wavelength), ns (nano-second), and fs (femtosecond) sources with center emission at about 800 nm (Ti:sapphire), 1200 nm (Cr:forsterite), 1400 nm (Cunyite), and 2000 nm to 10,000 nm (OPA) lasers may be used. Light sources include infrared lamps, LEDs, and lasers from 800-nm to 10000 nm. Light sources may be either continuous waves or pulsed. The pulse duration used may range from about 1-milliseconds to about 10 femtosecond. The repetition rate of this pulse can range from a single shot to about 1 GHz. The illumination light can be delivered to the sample site using free space or fiber delivery. The signal light can be collected from the sample site to the detector using free space lens imaging or fiber/lens collection.

Referring again to FIG. 1, using an optical parametric amplifier (OPA), ns and fs pulses with energies in the millijoule region and wavelengths >1,500 nm can be generated from a light source 24. Special photonic detection techniques, such as, Kerr gate, optical coherence tomography (OCT), and second harmonic tomography (SHGT) are employed in gate control 20 to obtain a depth resolution from about 0.1 micron to about 100 microns. Using the Kerr gate, the depth resolution limitation can be calculated from the product of the laser pulse duration used (e.g., $\sim10^{13}$s) and the speed of light in the medium (c/n$\sim 2\times10^8$ m/s). Using the OCT, SHGT, and other nonlinear optical techniques, the depth resolution may be limited by the focal depth of the imaging lens 26 used.

With the additional spectral information and polarization difference gating technique, the signal to noise ratio can be greatly enhanced to see through various thicknesses of paint.

Wavelength Dependence of Paints

Wavelength dependence is one key parameter for imaging defects under a painted surface (e.g., metal and dielectrics). Paints can be considered to be quasi-transparent for NIR wavelengths >800 nm. Factors to be considered in wavelength selection are: (a) minimal scattering for formation of sharp images, (b) optimal absorption to provide high-resolution images without extreme attenuation of image-bearing light, and (c) ability to detect key chemicals for functional monitoring of corrosion chemistry. The requirements of resolution, penetration, depth, diagnostic ability, and specificity to key chemicals of an optical imaging depend on the paint and the metal being investigated.

Figure 3A:
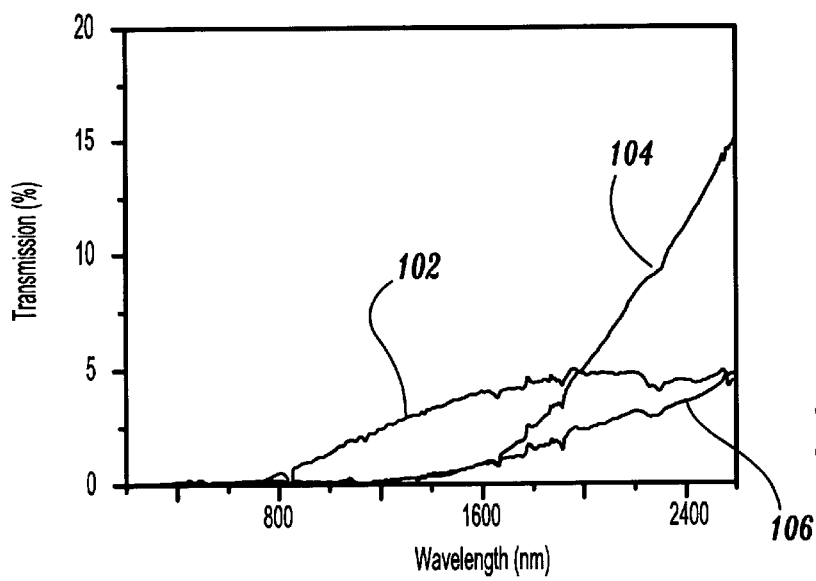
FIG. 3A depicts spectral transmission curves of different paints including a primer paint on a quartz plate, a blue paint on a quartz plate and a combined blue and primer paint on a quartz plate.
Figure 3B:
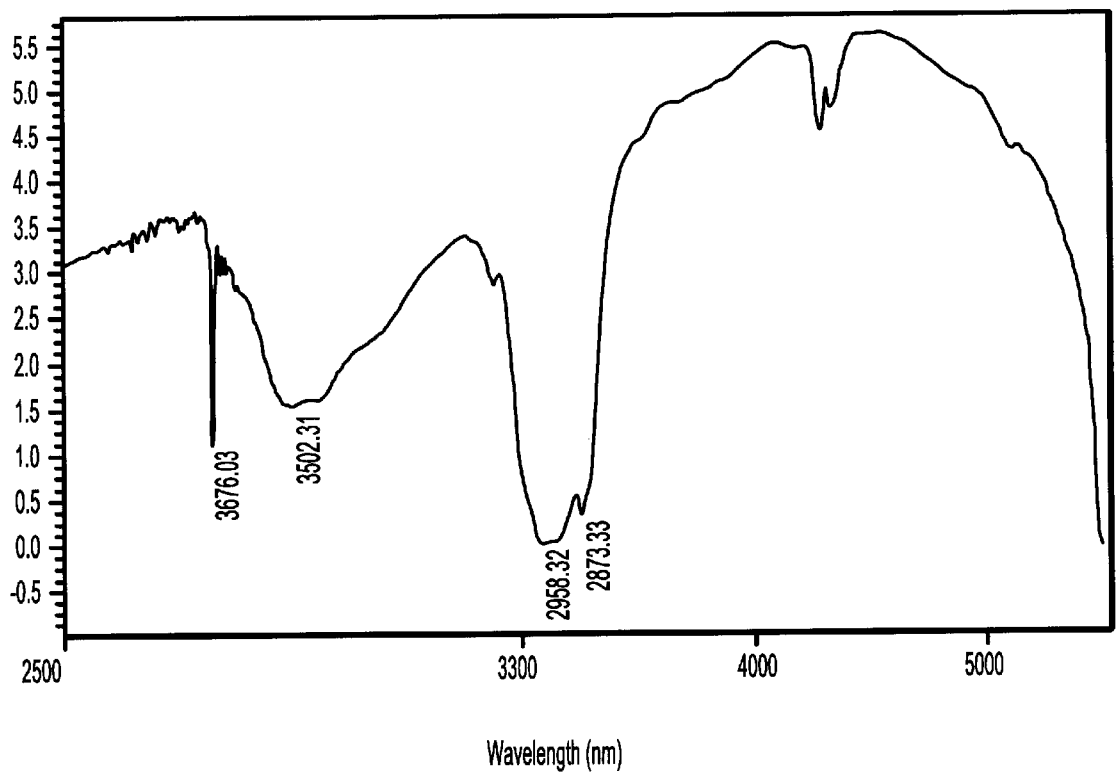
FIG. 3B depicts a spectral transmission curve for a combined blue/primer paint on a sapphire plate (transmission from 2500 to 5000 nm)

For example, using red paint, the light transmitted at 850 nm is greater than that from other wavelengths below 800 nm. Transmission spectra of three different paints are illustratively displayed in FIG. 3A. Transmission spectrum 102 is that of a primer paint on a glass plate. Transmission spectrum 104 is for blue paint on a glass plate, and transmission spectrum 106 is combined blue and primer paints on a glass plate. The transmittance between 800 and 1,200 nm is over 0.2%. Transmission through paints in the NIR region allows light to "see" metal conditions to determine whether there are any defects, corrosion, or cracking. In FIG. 3B, a transmission spectrum from 2500-nm to 5000-nm of a combined blue and primer paints on a sapphire plate indicates a broad high transmission ($\sim$5%) spectral window from 3600-nm to 5000-nm.

Ballistic Light Imaging

Figure 4:
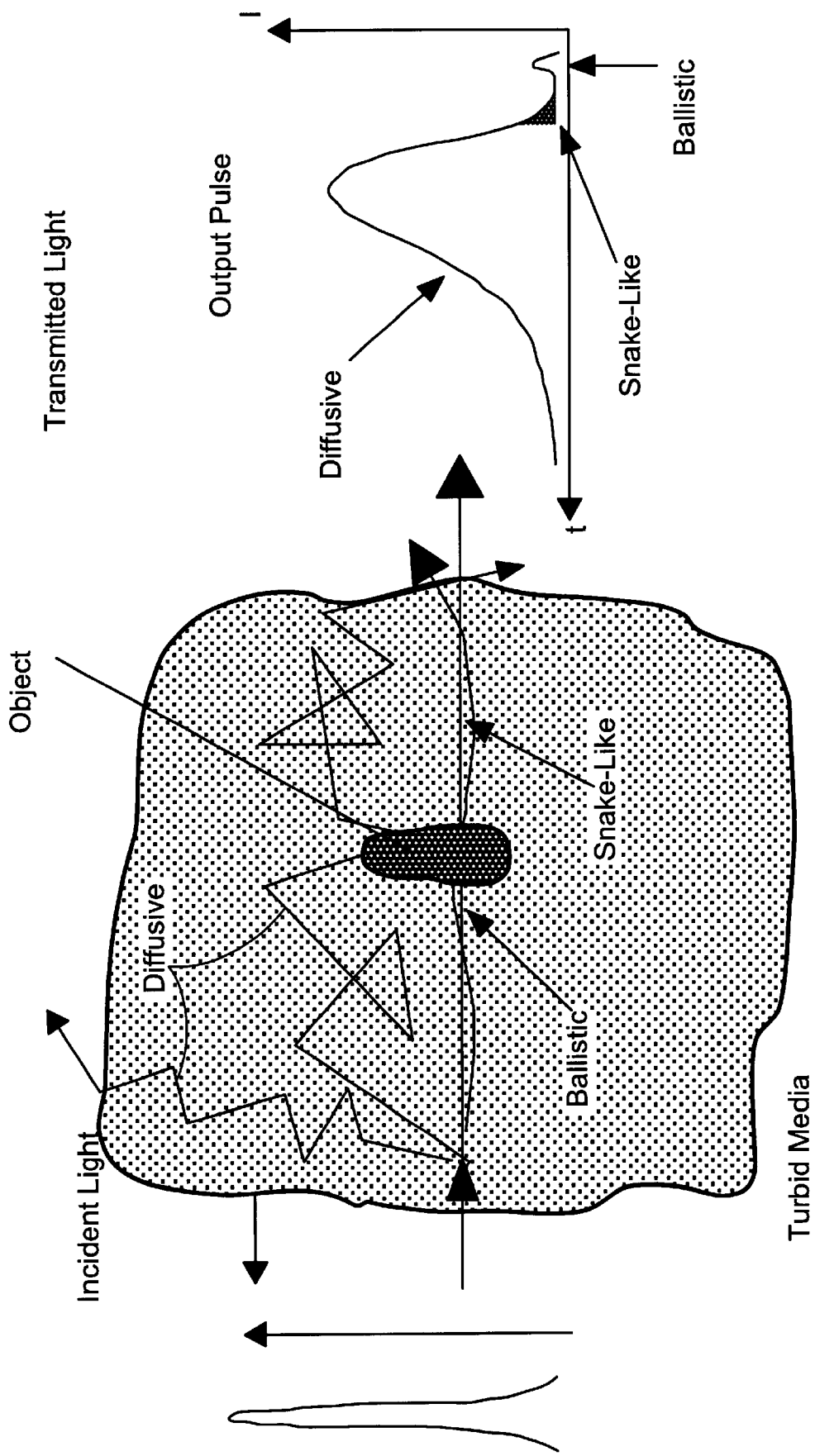
FIG. 4 is a schematic diagram showing ballistic, snake, and diffusive photon propagation in turbid media.

To provide ballistic light imaging, it is best to understand the nature of a light pulse propagating through turbid media (see the above references articles "Ballistic 2-D imaging through scattering wall using an ultrafast optical Kerr gate", and "Time-resolved imaging of translucent droplets in highly scattering media"). Characteristics of the incident light pulse-intensity, duration, coherence, and polarization change as the pulse is scattered inside the highly turbid medium, e.g., painted layer. The pulse that emerges from the medium has very different characteristics than that of the incident pulse. The transmitted pulse includes three temporal components: ballistic, snake and diffusive, as shown in FIG. 4. Similar concepts occur for back-scattered light reflected from metallic surfaces.

Diffusive light is the dominant component including multiple-scattered photons that travel the longest path, and are the last to exit the sample. Diffusive light carries little information about the internal structure of the medium. Ballistic photons (characterized by the scattering length $l_s$), traverse the shortest path, retain most characteristics of the incident photons, and carry direct information about the interior structure of the scattering medium. Snake photons (characterized by $l_t$), follow the ballistic light as they travel through the intervening medium, and arrive at the onset of the diffusive component. The trajectory of snake photons resembles a wriggling snake and hence the label 'snake'. Since snake photons are involved in fewer scattering events; they retain a significant amount of the initial properties and information on structures hidden in the scattering medium. In a highly scattering medium, the ballistic component is extremely weak while the diffusive component is the most intense. To form images of structures inside the turbid medium using ballistic and snake photons, diffusive photons should be reduced.

Gating Techniques

Several methods have been developed by the inventors to image inside scattering media at different depths. One approach is based on time gating. The principle behind time gating is that a 'camera' with an ultrafast shutter can be triggered to take a picture at the instant the ballistic and snake photons arrive. Gating control 20 of FIG. 1 provides this shutter control and exposure measurements. If the shutter closes fast enough, the delayed diffusive light will not be recorded. In practice, an exposure time of a few hundreds fs is needed to take such a picture with a sub-millimeter spatial resolution. The challenge is to develop an imaging system that is both fast and sensitive enough to capture the image. Time gating techniques may include an optical Kerr gate (OKG) (see, e.g., "Ballistic 2-D imaging . . . ", cited above, optical coherence tomography (see, e.g., "Ultrafast Correlation Interferometric Imaging through a Moving Scattering Medium", I. Zeylikovich, R. R. Alfano, Opt. Comm. 217 (1997)), and second harmonic generation cross-correlation gate tomography (see, e.g., "Second-harmonic Tomography", Yici Guo, P. P. Ho, H. Savage, D. Harris, P. Sacks, S. Schantz, F. Liu, N. Zhadin, R. R. Alfano, Opt. Lett. 22, 1323 (1997), each of these techniques was studied with $\sim$20 $\mu$m spatial resolution.

Another approach employs space gating. Since the diffusive light emerges from the scattering medium in all directions, a space gate can isolate the forward ballistic and snake light. A Fourier space gate, that uses a small aperture in the focal plane of the forward-light collecting lens to cut out the scattered light, was designed and successfully implemented. Coupling space and time gating, to further enhance the diffusive light rejection, was realized by combining an OKG with a Fourier gate.

Yet another approach is based on polarization gating. The polarization gate makes use of the fact that scattering events depolarize an incident beam of linearly polarized light so that ballistic photons retain their polarization state, while multiple-scattered photons are depolarized. In practice, a polarization gate is implemented by illuminating the object through a linear polarizer and collecting the emerging light through a second linear polarizer. The degree of polarization is defined as $(I_p-I_s)/(I_p+I_s)$ where $I_p$ and $I_s$ are transmitted light intensities with the axis of the second polarizer parallel and perpendicular to that of the first polarizer, respectively. It is used to select the image-bearing component since it is ideally expected to be unity for ballistic light and zero for completely depolarized light.

Absorption of light by a scattering medium may improve imaging performance through it. Since multiple-scattered light travels longer distances inside the medium than the image-bearing light, in an absorbing medium, the intensity of the multiple-scattered light will be reduced more than that of the image-bearing light. The challenge is to select light of a wavelength that is sufficiently absorbed by the medium to reduce the intensity level of the diffuse light below that of the image-bearing light, and thus improve the signal-to-noise ratio.

Photonics NDI techniques such as special polarization, second harmonic generation, and optical coherence tomography are advantageously employed, in accordance with invention, to measure corrosion and cracks at different depths beneath, for example, painted aircraft surfaces, letters within envelopes and artwork below coating materials. Other application include inspection of painted aircraft surfaces, airplane engines, rocket engines, interiors of metal or plastic tubes for fluids or gas delivery, metal structures of bridges, ship and submarine's body underneath water, automobile body, artworks, and security checking of written materials packed in envelopes. Written materials may include letters, graphics, pictures, printed matters within an envelope, etc. Artwork may include oil paints, water paints, masterpiece artwork, ancient artworks, Chinese water paint, Japanese water paint on canvas, wood, painted walls (wood, plywood, stone, drywall, sheet rock), plastic plates, metal, status, etc. Still other applications include preventive inspection of lottery tickets or other documents which require security protection to avoid illegal competitions, and detection of non-metallic phantoms embedded in metallic and dielectric surfaces or detection of information inside an envelope by imaging the paper overlay.

Polarization Difference Imaging (PDI)

Polarization properties of scattered light can be used to evaluate changes in matter. The spectral dependence of scattered light can be used to image corrosion beneath painted layers. An experimental set-up to detect corrosion beneath paint using spectral polarization imaging technique is illustratively shown in FIG. 5. Using the polarization property of NIR light to evaluate the local changes of materials beneath paints can be determined. Using a linearly polarized light to illuminate a sample (paint metal with corrosion), the state of the light back-scattered and reflected from the upper surface is partially polarized. The backscattered light from inside the paint at different depths becomes depolarized due to the scattering in the paint. This light is reflected back from the metal surface. The degree of polarization of the scattered light decreases when the distance that light travels through the paint increases. The polarization status of the light upon reaching the metal can be used for imaging corrosion or cracks in the metal at different depths beneath the paint. In addition to polarization, the spectral property of the scattered light can also be used to image corrosion beneath paint using the wavelengths ranging from about 800 nm to about 10,500 nm. Images are examined by rotating the first polarizer (P1) (FIG. 5) in front of the sample in parallel and perpendicular direction relative to the second polarizer (P2) (FIG. 5).

Referring to FIG. 5, a beam of a white light 202 (e.g., of diameter about 2 cm) illuminates a sample 204. Wide band filters (WBF) (550, 650, 750, and/or 850 nm) are used alternatively to select the desirable spectral range of illuminating light (in front of a white light source 201) and the scattered light 206 (in front of a camera 208, for example, a CCD camera). A first polarizer $P_1$ is located in the light beam pathway to obtain a linearly polarized illumination light with its polarization is orienting parallel and perpendicular to that of a second polarizer $P_2$ orientation. Second polarizer $P_2$ is positioned in front of camera 208 to detect the scattered light component from the sample 204. Camera 208 may include a cooled 16-bit CCD camera equipped with a zoom lens 210 of, for example, 50 mm focal length which is used to record the images.

Detail 1 shows a front view of sample 204 employed to demonstrate the PDI technique. A circular corrosion area 212 is induced by the reaction of a base solvent of potassium hydroxide on an aluminum plate 214. A bottom half of a circular corrosion area 212 and aluminum plate were painted with red color paint 216, which was 35 $\mu$m thick.

Referring to FIGS. 6A–D, images of sample 204 obtained through PDI show small change in the intensities of the scattered light from the bottom half of the circular corrosion area under different excitation wavelengths: $\lambda$=550, 650, 750, and 850 nm, shown respectively in FIGS, 6A, 6B, 6C and 6D. FIGS. 6A–D were taken with at an orthogonal polarization direction parallel to the incident field.

Referring to FIGS. 7A–D, it is clear from FIGS. 7A–D that the intensity of the scattered light from the bottom half of the corrosion area of sample 204 increases as the wavelength is increased, as shown by FIG. 7B, FIG. 7C and FIG. 7D. As the wavelength increases under different excitation wavelengths: $\lambda$=550, 650, 750, and 850 nm, shown respectively in FIGS, 7A, 7B, 7C and 7D, the light penetration is deeper and more information can be revealed about the corrosion beneath the paint. The results should be improved using wavelengths greater than 850 nm. FIGS. 7A–D were taken with at an orthogonal polarization direction perpendicular to the incident field.

Most of the parallel-scattered light comes from the upper half of the unpainted corrosion area as its surface facing the CCD camera is compared with the light from the bottom half, covered with paint. The images from FIG. 7 show that the intensities of the perpendicular scattered light from the bottom half of the circular corrosion area under different excitation wavelengths [e.g., $\lambda$=650, 750 and 850 nm] are higher than the perpendicular scattered ones from the upper half of the corrosion area. Similar results can be obtained from longer wavelengths, for example, 900 nm to 2000 nm, at high intensity. This increase is due to the scattered light from the bottom half of the corrosion area being more depolarized than that from the upper half. Photons from the bottom half are scattered more, since they undergo multiple scattering in the paint. The upper half photons suffer much less scattering. Since red paint does not transmit at 550 nm, the 550 nm trace (FIG. 7A) reveals the opposite observation where the perpendicular-scattered (also parallel scattered as shown in FIG. 6A) intensity from the bottom half of the corrosion is less than the upper half. The parallel images reflect the scattered signal from the surface, while the perpendicular images reflect the scattered signal beneath the surface.

Kerr-Fourier Gate (KFG) Imaging

A KFG is a combination of an optical Kerr time gate and a Fourier space gate (see, e.g., "Time-resolved Fourier spectrum and imaging in highly Scattering Media", L. Wang, P. P. Ho, R. R. Alfano, Appl. Opt. 32, 5043 (1993) and "Snake light tomography", P. P. Ho, L. Wang, X. Ling, L. L. Kapaxis, and R. R. Alfano, Optics & Photonics News, pp. 23–27, October (1993).

Figure 8:
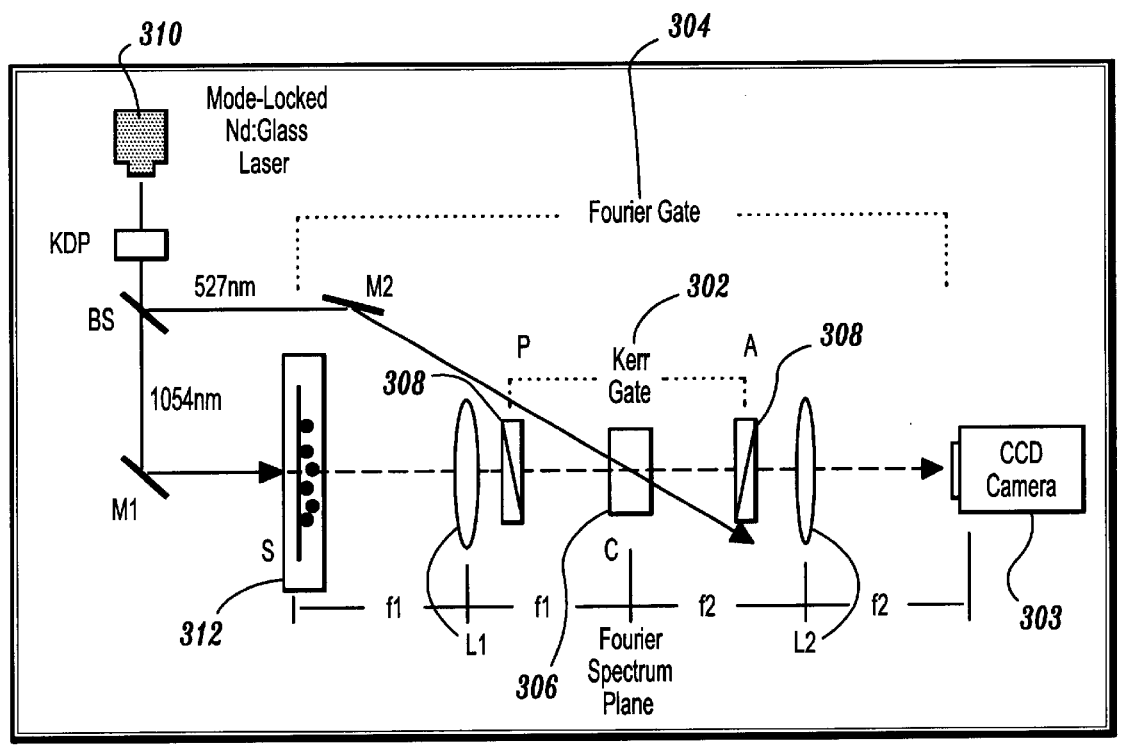
FIG. 8 is a schematic diagram of a picosecond optical Kerr gate for time-resolved image slicing in accordance with the present invention.

Referring to FIG. 8, an experimental arrangement for a KFG imaging system is illustratively shown. An optical Kerr gate 302 acts as an ultrafast shutter in a camera, that is triggered by an intense gating pulse, to take a picture the instant the image bearing light emerges and close thereafter to block diffusive light. A Fourier space gate 304 improves image contrast and dynamic range by spatially filtering out the higher spatial-frequency components of the image dominated by the diffusive light.

A Kerr cell 306 is placed between two calcite crossed polarizers 308. A new Kerr material, for example, Pb—Bi—Ga—doped glass with a femtosecond response, can be used for cell 306. A fraction of the energy from a fs laser system 310 illuminates a metal sample 312; the remaining fraction opens the Kerr gate 3023. The sample 312 and the Kerr cell 306 is placed at the back focal plane and the front focal plane, respectively, of a lens L1. Delay between the gating pulse and the reflected signal pulse is adjusted so that the early part of the signal pulse is transmitted through the Kerr gate 302. The transmitted signal is collimated by a lens L2 and directed onto a 16-bit CCD camera 303. This arrangement simultaneously acts as a Fourier gate with the interaction region of the gating and signal pulses within the Kerr Cell acting as the Fourier plane. The gate duration of this KFG is about 300 fs. Beam splitter BS and mirrors M1 and M2 are employed as is known in the art.

KFG is preferably combined with Fourier filtering, polarization gating, and the improvement of spatial mask filtering as a function of gating time to measure the thickness and corrosion/cracking size. A circular aperture may be employed in KFG imaging. For the signal through a random medium with different spatial frequencies, specially designed Fourier filters will be used to remove higher frequency noise background to enhance the presence of well defined structures. A particular structure/shape from the Fourier imaging mask can be used to separate corrosion from metal backscattered light. Various spatial masks of different dimensions, spatial shapes, and locations will be chosen in the time-sliced imaging system to improve the contrast of modeled lines in the early light image.

Figure 9:
FIG. 9 is a time-resolved Kerr image of calcium compound powders on a piece of glass slide immersed in the middle of a 50-mm thickness cell filled with milky water.

A result of KFG imaging of a layer of calcium compound deposits on a glass plate inside a turbid medium is displayed in FIG. 9 (see also, "Time-gated Images of Calcification Regions in Turbid Media", P. P. Ho, P. A. Galland, X. Liang, L. Wang, S. G. Demos, S. K. Gayen, R. R. Alfano, SPIE 2979, 94 (1997)). The glass slide with calcium compound deposits was placed in the middle of a (L=) 50 mm thick highly scattered medium characterized by $l_s(\lambda)$~2.5 mm. The image was recorded with the delay between the gating pulse and the signal pulse set equal. Dark spots in FIG. 9 are the images of calcium compound particles. These calcium particles could not be observed without time gating. Similar results should be imaged for painted samples with the following illustrative parameters: L=500 $\mu$m and $l_s$~25 $\mu$m, and $L/l_s$~20. In one illustrative embodiment, an aged oil painted artwork located beneath another painting on a same canvas can be imaged using the same procedure.

Using the Kerr-Fourier gating method, time sliced images are provided using temporal, polarization, spectral, and/or spatial information of the metal deterioration under paints. Ultrafast time gating is preferably used in tandem with a space gate or/and a polarization gate for better discrimination against scattered light. Performance and tradeoff points of polarizer-gated imaging with the fs time-spatial Kerr-Fourier imaging may be performed using, for example, an ultrafast Pb—Bi—Ga doped glass Kerr medium to optimize the measurements.

Optical Coherence Topography (OCT)

OCT is based on interference of broadband light, and will be used to image 3D corrosion layer structures with micron accuracy. Interference gives tomographic information of sub-surface micro structures with better than 10 $\mu$m depth-lateral resolution. Coherence properties associated with broadband light sources can be used as a gate to separate out backscattered light from the mismatched refractive index between corrosion and metal beneath paints, and down to depths of few hundred microns. Femtosecond resolution is accomplished using the coherence length associated with low-coherence broadband light. Due to the limited coherence length of the source, light returning from the interferometer reference arm, and light backscattered by the internal sample reflections, interfere only with the interferometer arm optical path lengths match to within the coherence length. With an appropriate NIR interference wavelength, several microns depth resolution of painted surfaces can be achieved.

Figure 10:
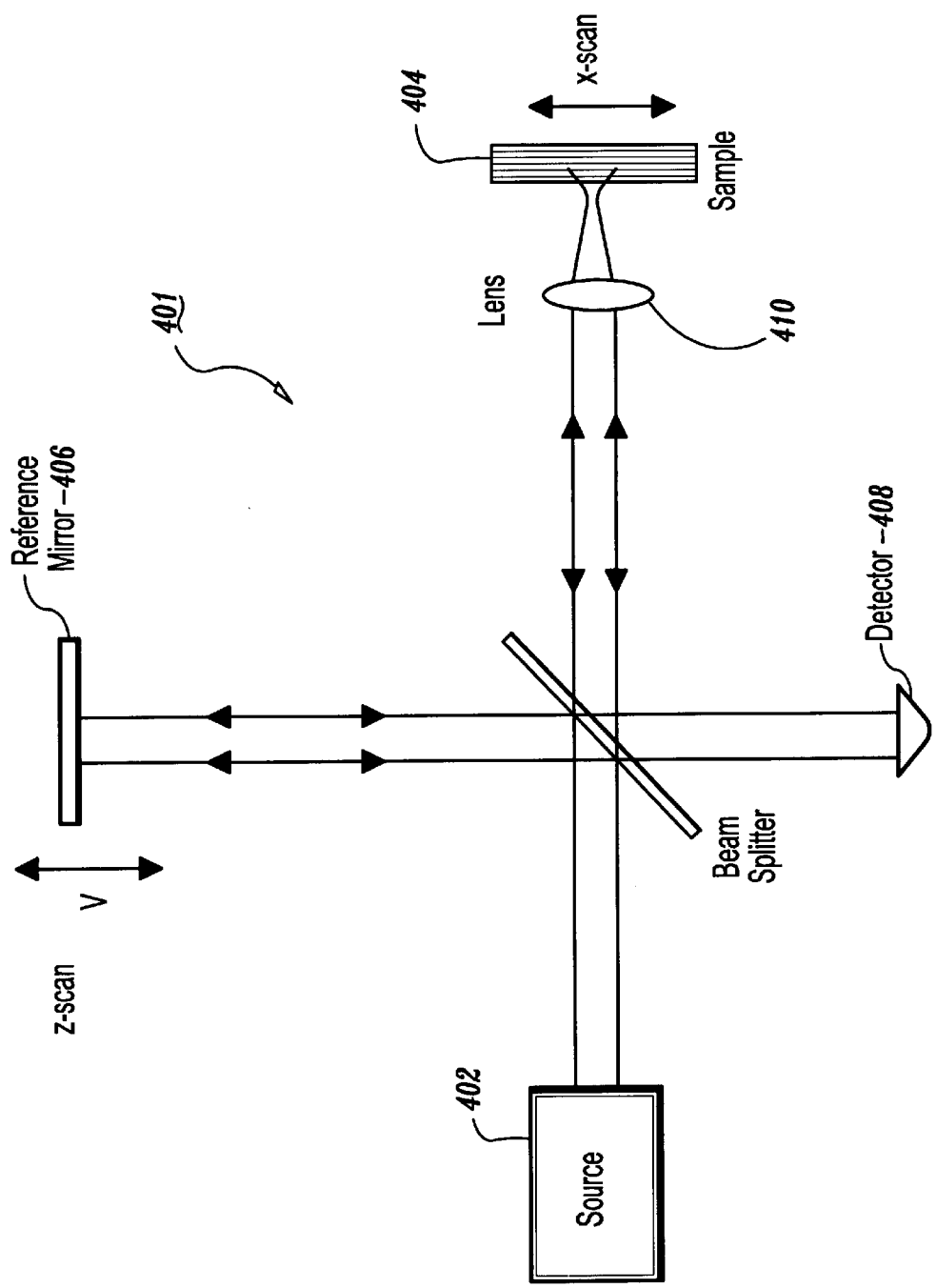
FIG. 10 is a schematic diagram of an optical coherence tomography setup in accordance with the present invention.

Referring to FIG. 10, an arrangement for employing OCT is illustratively shown. The arrangement makes use of a Michelson interferometer 401 with a broadband light source 402. One arm of the interferometer is replaced by a sample 404 under investigation. A reference mirror 406 is shifted with constant speed v to produce interference modulation with Doppler frequency $f_D=2v/\lambda$ for optical heterodyne detection, where $\lambda$ is the wavelength. Interference can occur at a detector 408 only when the path difference is less than the coherence length of the light source. The interferometric component of the detected signal is proportional to the square root of the sample reflectivity, which gives' the system very high sensitivity. Using heterodyne techniques to separate the low interferometric part of the signal from the high reference area intensity, very weak sample signals ($<10^{-12}\times$incident power) can be detected. Optical fibers are used in the interferometer to keep system stability and compatibility with the scanning elements.

To obtain 2D depth-lateral image of the object 404, the OCT system provides movement of the reference mirror 406 for scanning the depth direction, and movement of the beam focus by a lens 410 in the sample arm is provided for lateral scanning. Since the signal is acquired point by point, implementation of a fast scanning mechanism is one of the challenges in OCT. To achieve an image acquisition time less than 1 s, several new elements for modulation and translation have been introduced by the present invention, may include fast angular scanners, piezoelectric elements, fiber stretchers, etc. An OCT measurement of paint on glass has been demonstrated using an 850 nm superluminescent diode with about 10 $\mu$m resolution.

Resolution in depth or axial direction is determined by the coherence length of the light source. Broadband sources in wavelengths from, for example, 800 to 1500 nm, such as from superluminescent diodes, Ti-sapphire, Cr:YAG, and Cr:forsterite lasers, are available, providing resolution of 5–15 $\mu$m. Lateral resolution depends on numerical aperture of the objective 410 in front of the sample, but is also related to penetration depth.

OCT is used to measure paints with various thickness, for example, from about 30 microns to about 500 microns on metal. In one embodiment, measurements are made using both conventional OCT with a 10–20 $\mu$m coherence length and lateral resolution, and a 50 dB dynamic range and a grating-generated coherence microscope with 15 $\mu$m depth resolution/several microns lateral resolution and a dynamic range which is up to about 100 dB. The light sources with wavelengths from 800 nm to 5000 nm are preferably used to obtain spectral information from the OCT images of the corrosion to obtain optimized signals from the most suitable wavelength for imaging.

OCT may be employed using diffraction gratings to increase the data acquisition to a millisecond rate. This method converts the time propagation of pulses reflected from different depths in the object into a corresponding linear interference pattern that permits the simultaneous registration of reflections by a linear photodiode array without mechanical scanning.

In one embodiment, a reflection diffraction grating 411 will be installed in the Littrow configuration at the reference beam RB in FIG. 10. A cylindrical lens 410 is installed in the sample beam to illuminate a sample by a linear light source. The grating and sample surfaces will be optically focused into a 1024×104 pixel CCD array (detector) by the objective 410. The diffraction grating introduces a continuous optical delay (producing sample depth scan) in the direction of the grating dispersion (x axis). The difference of the optical path is $\Delta = 2 \sin \alpha = \lambda x/p$, where x is the linear coordinate along the grating surface, $\alpha$ is an angle between the normal to the grating and the reference beam. Different parts of the reference beam (it has the width of several mm) in x direction have different optical path lengths and they interfere with the beams backscattered from the different depths in the sample. The depth information from the sample is spread along the x direction on a CCD (detector). After acquisition of several images with different phase shifts and processing, a 2D depth-lateral image without any moving parts is obtained. The lateral resolution can be about 3-um and dynamic range up to 100 db with "16 bit" CCD camera. Signals as low as $10^{-10}$ of the incident power can be acquired.

The OCT system may use fiber optics, fs Ti: sapphire and Cr:forsterite lasers, an electronic processing system (see FIG. 11) to measure the output spatial frequency and the signal amplitude, and the depth-lateral imaging of painted metal with corrosion or cracking at different paint thickness. Using a grating OCT scan unit for filed application with diode laser and fiber optics to determine the depth-lateral scanning, resolution, dynamic range. The electronic processing system used with OCT determines the corrosion rate, signal level, signal-to-noise ratio, etc.

SHG Tomography (SHGT)

Another embodiment of the present invention employs nonlinear optical second harmonic generation (SHG) signals to produce sub-layer maps of corrosion under paint. SHG from corrosion or cracking of metal behind paint by an intense ultrashort laser pulse is preferably employed to map a spatial distribution of chemical components. When a sample is under intense short pulse light illumination, SHG can occur when two photons interact with the molecules simultaneously in the focal region of the incident beam. Either the sample or the incident laser beam is scanned to obtain 3-D tomographic images. Because the output SHG intensity, $I_{SHG} \sim I_{in}^2$ where $I_{in}$ is the input intensity, SHG outside the focal region is much weaker. Thus, the signals are highly localized resulting in the increase of image spatial resolution. SHG can provide local symmetry properties of metal corrosion and cracking. SHG is absent for regions of sample materials with isotropic symmetry. SHGT can penetrate deep through the paint with less scattering from the use of longer NIR photons as the incident beam. SHG coupled with scanning microscopy can yield submicron lateral resolution.

In one embodiment, SHG signals are generated from local regions having a lack of central-symmetry and/or from surface discontinuities at boundaries and interfaces of material deteriorations. Changes in the local symmetry produce additional amounts of SHG signals. Due to the strong nonlinear intensity dependence of SHG signals (proportional to $I^2$), the focal region can be at micron size to produce a 3D topographic map of the paint-metal layers. The primary and SHG wavelengths are in the transmission zone of the paint to image the metal corrosion region. For example, a primary wave at 2000 nm will produce 1000 nm SHG signals from metal-paint interface to detect any corrosion which gives additional amount of SHG intensity. Both primary and SH wavelengths at the focal plane are collected by the lens, and the primary photons can be easily removed by a narrow band filter to achieve excellent S/N ratio.

In one embodiment, different laser sources may be used, e.g., Cunyite (1400 nm), Cr:YAG(1500 nm), and Ti-sapphire. OPA (tunable from 800 nm to 5000 nm) lasers to produce ED SHGT of corrosion distribution of metal with an overcoat of painted layers. Wavelengths of >about 1600 nm .may be employed as the primary wavelength for SHGT method to detect layered information in paints and beneath paints. Different focal lengths of NIR microscopic objective lenses may be employed with different depth of field to obtain different depth spatial resolutions from 0.1 microns to 100 microns.

Figure 11:
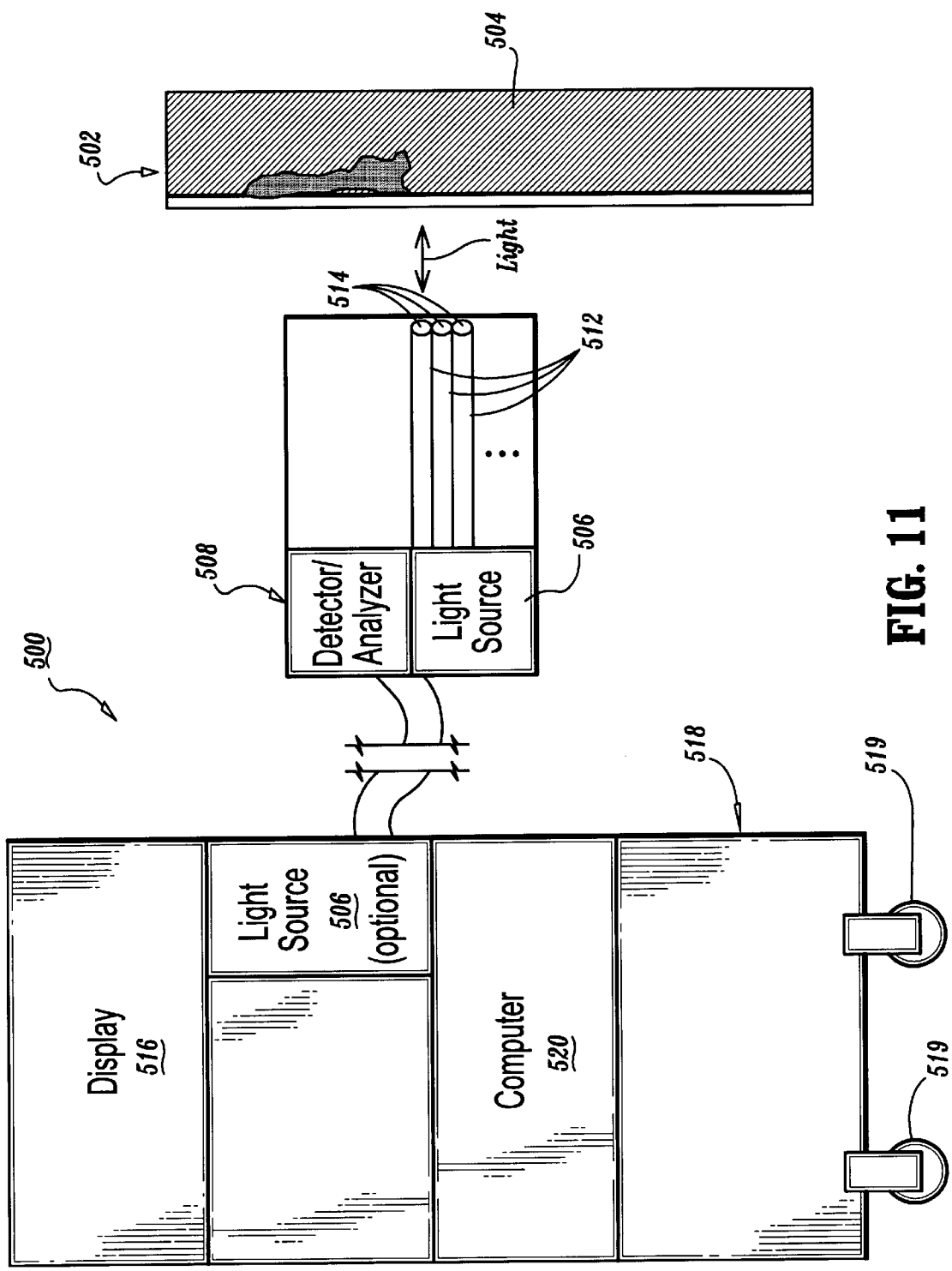
FIG. 11 is a schematic diagram showing an apparatus for non-destructive imaging in accordance with the present invention.

A hand-held head of SHGT may be made by incorporating optical fibers into the imaging system (see FIG. 11). Laser light is coupled into a fiber in a fiber bundle. A micro-lens at the end of bundle tip is used to focus light into the paint or coating. The SHG signals are collected by other fibers in the bundle and relayed to a photo-detector. Different types of scanners, piezoelectric, gavionmetric, opto-mechanical approaches may also be used to probe painted surfaces for defects.

Referring again to FIG. 1, an experiment using SHGT employs the set-up shown in FIG. 1. SHGT of a painted corroded steel plate (e.g., metal 14) was obtained by directing a fs laser beam (10) at 800 nm into the sample using a dichroic beam splitter (32) and a microscope objective (26). The dichroic beam splitter (32) reflected the excitation laser light while transmitting the SHG signal generated to the painted metal sample. The SHG signal was collected by the same objective (26) and transmitted through the dichroic beam splitter (32). The SHG signal was then collected by relay optics to a photo-detector in gate control 20. To image sub-surface of painted metal, the focal region was scanned into the metal 14 by moving sample 15 with translation stages (not shown). A series of measured SHG images from a corrosive steel plate under paint is illustratively displayed in FIG. 2. These images may be employed to create 3-D maps or images 35. In one embodiment, laser wavelengths from about 1200 nm to about 5000 nm may be employed to penetrate painted layers and the output SHG signals at about 600 nm to about 2,500 nm can pass through the upper layers of paints and employed for imaging.

Optimum spectral regions may be used for in-situ measurement, and to study the difference in SHG between various paints, corrosion, and metals. SHG symmetry maps and chemical content maps may be correlated to obtain and to understand additional characteristics of corrosion. For example, chemical properties of the corrosion, the corrosion rate as a function of the corrosion depth can be studied from the SHGT by comparing the data obtained from different corrosion times.

Referring to FIG. 11, an apparatus 500 for measuring defects or deterioration underlying paint layers or other coatings is illustratively shown in accordance with the present invention. A sample 502 is to be inspected by one or methods of the present invention. Using NIR wavelengths from about 800 nm to about 10,000 nm non-destructively detection of deterioration, corrosion and/or cracking of metal under paints, documents within an envelope, or artwork which have been painted over may be detected. Differences of optical scattering coefficients are employed to separate original metal 504 of sample 502 from the corroded area or cracking portions 506. In preferred embodiments, deteriorated information of metal under the thickness of painted films from about 0.1 microns to about 1000 microns can be revealed using polarization gating (PDI), spatial gating (SHGT), time gating (KFG), coherence gating (OCT), and nonlinear optical gating (SHGT).

Sample 502 may be part of, for example; painted aircraft surfaces, airplane engines, rocket engines, interiors of metal or plastic tubes for fluids or gas delivery, metal structures of bridges, ship and submarine's body underneath water, automobile body, artworks, and security checking of written materials packed in envelopes. Metal 504 may include steel, stainless steel, iron, aluminum, nickels, titanium, copper, brass, tin, lead, zinc, chromium, gold, silver, platinum, alloys or combinations of these elements, or any other suitable metal. Other materials may be analyzed instead of metal 504, for example, artwork or written materials may be detected through a dispersive media, such as paper, paint, dielectric, etc. Written materials may include letters, graphics, pictures, printed matters within an envelope, etc. Artwork may include oil paints, water paints, masterpiece artwork, ancient artworks, Chinese water paint, Japanese water paint on canvas, wood, painted walls (wood, plywood, stone, drywall, sheet rock), plastic plates, metal, statues, etc.

Apparatus 500 may also be employed to preventively inspect lottery tickets or other documents which require security protection to avoid illegal competitions. Non-metallic phantoms embedded in metallic and dielectric surfaces may also be detected.

Apparatus 500 includes a light source 506, with light preferably being delivered from a handheld unit 508. Light sources 506 may include infrared lamps, LEDs, and lasers from 800 nm to 10000 nm. Light sources may be either continuous waves or pulsed. The pulse duration used may be in a range from about 1 millisecond to about 10 femtoseconds. The repetition rate of this pulse may range from single shot to 1 GHz. The illumination light form light source 506 may be delivered to the sample site using free space or delivery by an optical fiber 512. The signal light can be collected from the sample 502 to the detector using a lens 514, which may include a free space lens or fiber/lens collection to provide an image.

Apparatus 500 may be employed to determine corrosion rate by measuring depth of corrosion to obtain the rate of corrosion formation of metal in air, liquids, or under paints. The corrosion rate which can be expressed as CR (mils/year)=534×Weight)/Density×Area×Time)~ Depth of Corrosion, is one key parameter to estimate the life of the airplane or equipment after corrosion. 3D sliced NDI methods (KFG, OCT, and SHGT) may be used to determine the depth or corrosion rate of target samples.

Apparatus 500 includes a display 516 for displaying image data. In one example, display includes a field of 1000×1000 pixels to display 1 Megabyte of information. In this example, 1 Megabyte of information may be collected from an area of about 1"×1" per second on an in-situ computer monitor in a quasi-real time mode. Resolution and area displayed may be modified accordingly. For example, a continuous light (cw) source and spectral imaging may be employed to image an area about 3 ft ×3 ft with a resolution that depends on a focal plane array. Larger areas may also be imaged. For example, using ultrafast time gating, an imaging or scanned area of 12'×12' can be acquired at a rate of about 1"×1" per second with a spatial resolution of about 0.001".

Hand-held optical detection head or unit 508 is preferably coupled to a movable cart 518. Cart 518 may house light source 506, such as a laser source and a processing device, such as a computer 520. Preferred dimensions of cart 518 are approximately 3'×3'×3' and cart 518 may be mounted on rollers 519 for easy transportation. Regular household 120V/15A electrical power is preferably used. System is safe for the operator under normal operation usage. Apparatus 500 includes an analyzer or detector 522. Analyzer 522 provides imaging components or elements, which are needed to employ the analysis techniques described herein. For example, a camera, lens', gates, polarizers, etc. Camera for analyzer 522 or any other detector or camera referred to herein may include a CCD, CID or CMOS based (e.g., imager chip) camera or device.

It is to be understood that the elements of apparatus 500 may be miniaturized into a single handheld device to analyze defects, etc. in accordance with the present invention. It is also to be understood that apparatus 500 may be employed to optimize wavelength zones based on available detectors and laser sources, and sample scattering and absorption properties. For example, scattering length $l_s(\lambda)$, transport length $l_a(\lambda)$ from various painted metal and glass substrates may be determined with various thickness of paints or coatings using transmission and back-scattered ballistic components. Apparatus may include an imaging system which images discrete wavelengths of light, for example, a polarization-gated imaging system may be provided using different NIR wavelengths (e.g., 800, 1200, 1500, 2000 nm, . . . up to 10000 nm).

Other optimizations may include measuring dynamic ranges of a polarizer spectral gate system (for PDI) to provide improved signal to noise ratio and contrast appropriately selected wavelengths. Further, characteristics of paints, metals, corrosion, cracking, etc. may be characterized by comparing spatial resolution and contrast of snake photons for the first 100 ps time slice, using both cw and fs pulse measurements or determining limitations of ballistic light imaging as a function of wavelength and depth of painted layers.

Other uses include: providing time sliced back-scattered images which may be used to reconstruct a 3D image of painted surfaces using reflected and scattered temporal profiles from various paints using fs pulses and fs detection methods; determining polarized and depolarized images with and without corrosion areas using light in the wavelength range 800 to 10,000 nm.

THE present invention may employ combinations of light measuring techniques. For example, the PDI method may be combined with OKG and SHGT to study the improvement of sensitivity and dynamic-range or the OKG may be coupled with PDI to enhance the overall performance for the contrast and depth of penetration.

Figure 12:
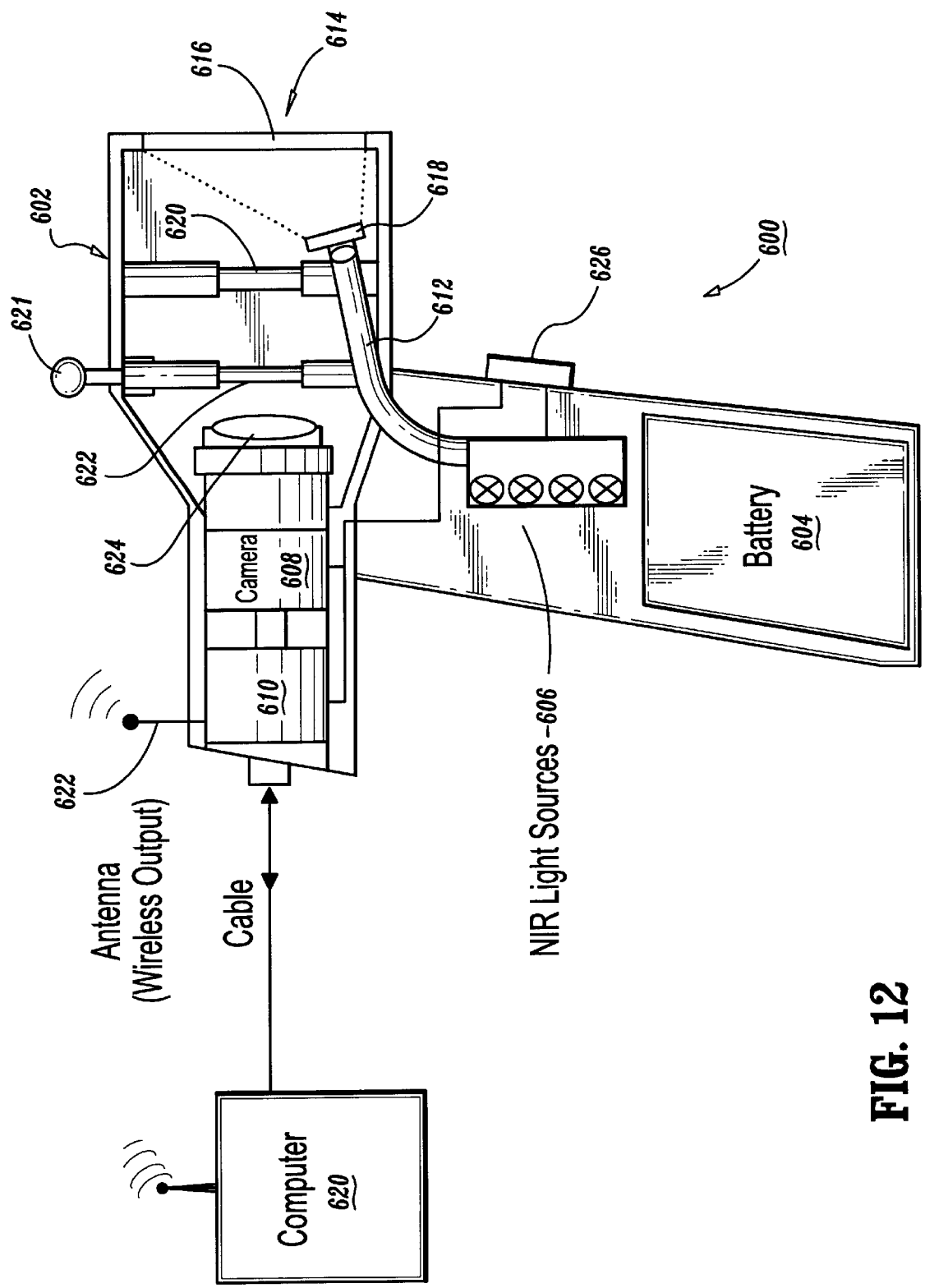
FIG. 12 is a schematic diagram showing a hand-held unit for non-destructive imaging in accordance with the present invention.

Referring to FIG. 12, a portable hand-held unit 600 includes a housing 602 configured and dimensioned for portable hand-held operation. A battery 604 or other power source are included to supply power to NIR light sources 606, camera 608 and transmitter/control panel 610. Camera 608 may include photodetectors, a CCD, CID or CMOS based (e.g., imager chip) camera. Light sources 606 provide NIR light via optical fiber 612 to a window 614. Window 614 may be covered by a cover glass 616 to protect internal components. In one embodiment, a polarizer 618 is attached to the end of fiber 612 to polarize light for light sources 606. Light reflected back to unit 600 is received through optical component(s) 620. Optical component 620 may include diffraction gratings, polarizers, lens', filters, etc. Another polarizer 622 or optical component may be included (for the PDI technique) and a control handle 621 may be provided to adjust polarizer 622. A lens 624 focuses incoming light into camera 608. Control panel 610 includes a memory buffer, an image processing hardware or software, such as image compression routines or chips, imager chip, etc. Other communication software or protocols are stored in transmitter/control panel 610 as well.

Panel 610 provides an interface between a computer or processing device. Panel 610 may include wireless capabilities or a cable interface to a personal computer, for example. The computer would then provide the image processing needed for displaying an image of the sample being inspected. A control switch 626 is provided to permit activation of light sources 606 and camera 608. Image processing may be performed by devices or software included in control panel 610 or may be performed on a computer 620. Image processing may include techniques known in the art. Unit 600 may be coupled to computer 620 by a plurality of different techniques. In one useful embodiment, a wireless connection is made to computer 620 through a transceiver employed on panel 610. An antenna 622 is employed to send and receive signals. Other known methods may also be employed.

Having described preferred embodiments for sub-surface imaging under paints and coatings using early light spectroscopy (which are intended to be illustrative and not limiting), it is noted that modifications and variations can be made by persons skilled in the art in light of the above teachings. It is therefore to be understood that changes may be made in the particular embodiments of the invention disclosed which are within the scope and spirit of the invention as outlined by the appended claims. Having thus described the invention with the details and particularity required by the patent laws, what is claimed and desired protected by Letters Patent is set forth in the appended claims.

What is claimed is:

1. A system for non-destructively imaging surfaces through a coating, comprising:
    a near-infrared (NIR) light source for illuminating a coated surface;
    a detector positioned in an operative relationship with the NIR light source to receive early backscattered light from the coated surface and from the coating; and
    a gating device positioned in an operative relationship with the detector to selectively permit the early backscattered light to, pass to the detector to measure optical characteristics of the early backscattered light such that determinations of a state of a surface below the coating is determined based on the optical characteristics of the early backscattered light.

2. The system as recited in claim 1, wherein the NIR light sources provide light having a wavelength between about 800 nm to 10,000 nm.

3. The system as recited in claim 1, wherein the determinations of the state of the surface includes determinations of stages of one or more of deterioration, corrosion and cracking.

4. The system as recited in claim 1, wherein the optical characteristics include different optical scattering coefficients for an undamaged surface and a damaged surface.

5. The system as recited in claim 1, wherein the surface includes a metal.

6. The system as recited in claim 1, wherein the coating includes paint.

7. The system as recited in claim 1, wherein the coating includes a thickness of between about 0.1 microns to about 1,000 microns.

8. The system as recited in claim 1, wherein the gating device includes one of a polarization gating (PDI) device, a spatial gating (SHGT) device, a time gating (KFG) device, a coherence gating (OCT) device, and a nonlinear optical gating (SHGT) device.

9. The system as recited in claim 8, wherein the polarization gating device includes polarization difference imaging (PDI).

10. The system as recited in claim 8, wherein the spatial gating device includes second harmonic gating tomography (SHGT).

11. The system as recited in claim 8, wherein the time gating device includes a Kerr-Fourier gate(KFG).

12. The system as recited in claim 8, wherein the coherence gating device includes optical coherence tomography (OCT).

13. The system as recited in claim 8, wherein the nonlinear optical gating device includes second harmonic gating tomography.

14. The system as recited in claim 1, wherein the coated surface includes graphics, and wherein the system is used for deciphering the graphics.

15. The system as recited in claim 14, wherein the graphics include letters, pictures, printed matters and the coating includes paper.

16. The system as recited in claim 14, wherein the graphics includes artwork.

17. The system as recited in claim 1, wherein the NIR light source includes one of an infrared lamp, a light emitting diode and a laser.

18. The system as recited in claim 1, wherein the NIR light from the light source includes one of a continuous wave source and a pulsed source.

19. The system as recited in claim 1, wherein the pulsed source includes one of a nanosecond, picosecond and femtosecond pulse source.

20. The system as recited in claim 1, wherein the detector includes a camera.

21. The system as recited in claim 1, further comprising a display device for imaging the light received at the detector through the gating device.

22. The system as recited in claim 1, further comprising a hand-held optical detection head configured to adjust light transfer to and from a coated surface to be imaged.

23. The system as recited in claim 1, further comprising a processor coupled to the gating device and the detector for providing the gating and image processing.

24. The system as recited in claim 1, wherein the optical characteristics include transport length, $l_t(\lambda)$, scattering coefficients, $l_s(\lambda)$, and absorption coefficients, $l_a(\lambda)$.

25. The system as recited in claim 24, wherein the light from the NIR source includes ballistic light and the optical characteristics are measured for the ballistic light.

26. The system as recited in claim 24, wherein the optical characteristics, $l_t(\lambda)$, $l_s(\lambda)$, and $l_a(\lambda)$, are determined as a function of wavelength.

27. The system as recited in claim 1, wherein the optical characteristics include at least one of temporal, polarization, spectral, and spatial information obtained from the backscattered light.

28. A method for non-destructively imaging surfaces covered by a coating, comprising the steps of:
    irradiating a coated surface with near-infrared light to provide backscattered light from the coating and the coated surface;
    gating the backscattered light to selectively permit early light to pass to a detector; and measuring optical characteristics of the early light received by the detector to image the coated surface below the coating to determine if damage exists on the coated surface.

29. The method as recited in claim 28, wherein the NIR light includes a wavelength between about 80 nm to 10,000 nm.

30. The method as recited in claim 28, wherein the damage to the coated surface includes one or more of deterioration, corrosion and cracking.

31. The method as recited in claim 28, wherein the step of measuring optical characteristics includes the step of determining differences in optical scattering coefficients an undamaged coated surface and a damaged coated surface.

32. The method as recited in claim 28, wherein the coated surface includes a metal.

33. The method as recited in claim 28, wherein the coating includes paint.

34. The method as recited in claim 28, wherein the coating includes a thickness of between about 0.1 microns to about 1,000 microns.

35. The method as recited in claim 28, wherein the step of gating includes one of a polarization gating, a spatial gating, a time gating, a coherence gating, and a nonlinear optical gating.

36. The method as recited in claim 35, wherein the polarization gating includes polarization difference imaging (PDI).

37. The method as recited in claim 35, wherein the spatial gating includes second harmonic gating tomography (SHGT).

38. The method as recited in claim 35, wherein the time gating includes a Kerr-Fourier gate (KFG).

39. The method as recited in claim 35, wherein the coherence gating includes optical coherence tomography (OCT).

40. The method as recited in claim 35, wherein the nonlinear optical gating includes second harmonic gating tomography.

41. The method as recited in claim 35, wherein the coated surface includes graphics, and the method further comprises the step of deciphering the graphics.

42. The method as recited in claim 41, wherein the graphics include letters, pictures, printed matters and the coating includes paper.

43. The method as recited in claim 41, wherein the graphics includes artwork.

44. The method as recited in claim 28, wherein the step of irradiating includes providing NIR light for a light source, which includes one of an infrared lamp, a light emitting diode and a laser.

45. The method as recited in claim 28, further comprising the step of displaying an image of the backscattered light to determine damage to the coated surface.

46. The method as recited in claim 45, further comprising the step of rendering a three-dimensional image of the coated surface.

47. The method as recited in claim 28, further comprising the step of processing the backscattered light to provided an image of the coated surface.

48. The method as recited in claim 28, wherein the optical characteristics include transport length, $l_t(\lambda)$, scattering coefficients, $l_s(\lambda)$, and absorption coefficients, $l_a(\lambda)$.

49. The method as recited in claim 28, wherein the NIR light includes ballistic light and the step of measuring optical characteristics includes measuring the optical characteristics of backscattered ballistic light.

50. The method as recited in claim 28, wherein the optical characteristics include at least one of temporal, polarization, spectral, and spatial information obtained from the backscattered light.

51. The method as recited in claim 28, wherein the step of measuring includes the step of if corrosion exists on the coated surface, measuring a depth of corrosion to determine a corrosion rate.

52. The method as recited in claim 28, wherein the step of irradiating is performed by a light source which includes one of a nanosecond, picosecond and femtosecond laser source.

* * * * *